US00PP36231P2

(12) United States Plant Patent
Guo

(10) Patent No.: US PP36,231 P2
(45) Date of Patent: Oct. 29, 2024

(54) ***KALANCHOE* PLANT NAMED 'KLEKB20035'**

(50) Latin Name: *Kalanchoe blossfeldiana*
Varietal Denomination: KLEKB20035

(71) Applicant: KLEMM + SOHN GMBH & CO. KG, Stuttgart (DE)

(72) Inventor: Huijuan Guo, Kornwestheim (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/600,179

(22) Filed: Mar. 8, 2024

(51) Int. Cl.
*A01H 5/02* (2018.01)
*A01H 6/32* (2018.01)

(52) U.S. Cl.
USPC ..... Plt./340
CPC ..... *A01H 6/324* (2018.05)

(58) Field of Classification Search
USPC ..... Plt./340
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Kalanchoe* plant particularly distinguished by semi double, orange flowers with a darker orange center, is disclosed.

1 Drawing Sheet

Genus and species: *Kalanchoe blossfeldiana.*
Variety denomination: 'KLEKB20035'.

BACKGROUND OF THE NEW PLANT

The present invention comprises a new and distinct variety of *Kalanchoe*, botanically known as *Kalanchoe blossfeldiana* and hereinafter referred to by the variety name 'KLEKB20035'. 'KLEKB20035' originated from a controlled-cross between the proprietary female *Kalanchoe* variety 'Don Amarillo' (unpatented) and the proprietary male *Kalanchoe* variety 'Lipstick' (unpatented).

In May 2017, the two *Kalanchoe* parental lines, the proprietary female *Kalanchoe* variety 'Don Amarillo' and the proprietary male *Kalanchoe* variety 'Lipstick' were crossed in De Lier, Netherlands and seeds were obtained. The seeds were sown and plants were grown for evaluation. A single plant was selected in June 2019 and subsequently named 'KLEKB20035'. In July 2019 'KLEKB20035' was first vegetatively propagated by vegetative terminal cuttings in Stuttgart, Germany. 'KLEKB20035' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Semi double, orange flowers with a darker orange center.

DESCRIPTION OF THE PHOTOGRAPH

This new *Kalanchoe* plant is illustrated by the accompanying photograph which shows an overall view of the plant. The photograph is of an approximately 12-week-old plant grown in Stuttgart, Germany in October 2023. The colors shown are as true as can be reasonably obtained by conventional photographic procedures.

DESCRIPTION OF THE NEW VARIETY

The following detailed descriptions set forth the distinctive characteristics of 'KLEKB20035'. The data which define these characteristics were collected from asexual reproductions carried out in Stuttgart, Germany. Data was collected on plants grown 19-weeks in Stuttgart, Germany grown in a greenhouse in February 2024. Color references are to The R.H.S. Colour Chart of The Royal Horticultural Society of London (R.H.S.), $5^{th}$ edition (2007).

Classification:
- *Family.*—Crassulaceae.
- *Botanical.—Kalanchoe blossfeldiana.*
- *Designation.*—'KLEKB20035'.

Parentage:
- *Female parent.*—'Don Amarillo' (unpatented).
- *Male parent.*—'Lipstick' (unpatented).

Propagation:
- *Type.*—By vegetative terminal cuttings.
- *Time to initiate roots, summer.*—About ten days at temperatures about 20° C.
- *Time to initiate roots, winter.*—About twelve days at temperatures about 20° C.
- *Time to produce a rooted young plant, summer.*—About three weeks at temperatures about 20° C.
- *Time to produce a rooted young plant, winter.*—About four weeks at temperatures about 21° C.
- *Root description.*—Fine, fibrous, typically greyish white in color, actual color of the roots is dependent on substrate composition, water quality, fertilizer type and formulation, substrate temperature and physiological age of roots.
- *Rooting habit.*—Moderately freely branching.

Plant description:

*Plant and growth habit*.—Medium vigor, upright, uniformly mounded plant habit; freely flowering with numerous cymes positioned above the foliar plane; Triangular in shape with rounded crown; 6 to 14 cm containers; moderately growth habit.

*Plant height at flowering*.—26 cm.

*Plant diameter at flowering*.—22 cm.

*Branching habit*.—freely branching habit with about fifteen lateral branches developing per plant.

*Lateral branch description*.—Length: 7 to 14 cm. Diameter: 7 cm. Internode length: 1.0 cm. Aspect: Mostly upright. Strength: Moderately strong. Texture: Smooth, glabrous. Color: Developing: RHS 143A. Developed: RHS 143C.

Leaf description:

*Arrangement*.—Opposite, single, generally symmetrical.

*Quantity of leaves per lateral branch*.—1-4 pairs.

*Length*.—About 11 cm.

*Width*.—About 8.5 cm.

*Shape*.—Ovate.

*Apex*.—Obtuse.

*Base*.—Obtuse.

*Margin*.—Broadly crenate.

*Texture*.—Upper surface: Smooth, glabrous, coriaceous, succulent, glossy. Lower surface: Smooth, glabrous, coriaceous, succulent, matte.

*Venation pattern*.—Pinnate.

*Color*.—Developing leaves: Upper surface: RHS 147A. Lower surface: RHS 137A. Fully developed leaves Upper surface: RHS 139A. Lower surface: RHS N138B.

Petioles:

*Length*.—0.3 to 1.5 cm.

*Diameter*.—0.3 to 0.6 cm.

*Strength*.—Strong.

*Texture*.—Smooth, glabrous, coriaceous, succulent.

*Color*.—Upper surface: RHS 139B. Lower surface: RHS 138B.

Flower description:

*Flower arrangement and habit*.—Semi double type flowers arranged in axillary cymes; uniform and freely flowering habit, continuously for 6-7 weeks.

*Fragrance*.—Absent.

*Natural flowering season*.—Initiate and develop flowers under short day/long night conditions or during November and December in the Northern Hemisphere; buds and flowers can also be induced under artificial short day/long night conditions with around 14 hours darkness.

*Time to flower*.—Medium early flowering habit, plants begin flowering around 13 weeks after potting.

*Post-production longevity*.—Good post-production longevity, plants maintain good foliage and flower substance.

*Flower diameter*.—2.0 cm.

*Flower length* (*height*).—1.6 cm.

*Flower bud*.—Length: 1.5 cm. Diameter: 0.4 cm. Shape: Initially oblong, becoming tubular ovoid with development. Texture: Smooth, glabrous, glossy. Color: RHS 25B, RHS 55B in later phase of the buds.

Petals:

*Arrangement*.—About 13-15 petals in multiple whorls.

*Length*.—0.8 cm.

*Width*.—0.5 cm.

*Aspect*.—Flat.

*Shape*.—Ovate to round.

*Apex*.—Acute.

*Base*.—Obtuse.

*Margin*.—Entire.

*Texture*.—Upper surface: Smooth, glabrous, glossy. Lower surface: Smooth, glabrous, glossy.

*Color*.—When opening: Upper surface: RHS N25B. Lower surface: RHS 33A. Fully opened: Upper surface: RHS 25B, base RHS 33A. Lower surface: RHS 33A.

Sepals:

*Appearance*.—Four in a single whorl.

*Length*.—0.6 to 0.8 cm.

*Width*.—0.15 cm.

*Shape*.—Oblong, pointed.

*Apex*.—Acute.

*Base*.—Obtuse.

*Margin*.—Entire.

*Aspect*.—Upright.

*Texture*.—Upper surface: Smooth, glabrous, glossy. Lower surface: Smooth, glabrous, glossy.

*Color*.—Upper surface: RHS 143A. Lower surface: RHS 143B.

Peduncles:

*Length*.—0.4 cm.

*Diameter*.—0.1 cm.

*Aspect*.—Erect.

*Strength*.—Strong.

*Texture*.—Smooth and glabrous.

*Color*.—RHS N137C.

Reproductive organs:

*Androecium*.—Stamen number: Around eight per flower. Filament color: RHS N144B. Anther length: 0.1 cm. Anther shape: Elliptic. Anther color: RHS N137A. Amount of pollen: Scarce. Pollen color: RHS 12A.

*Gynoecium*.—Pistil number: 3 to 4. Pistil length: 1.0 cm. Style length: 0.4 cm. Style color: RHS 141D. Stigma color: RHS 141D. Ovary color: RHS 141C.

Seeds:

Quantity per flower: If developed, up to 20 seeds.

Length: About 0.01 cm.

Diameter: About 0.05 cm.

Texture: Rough.

Color: RHS 166B.

Temperature tolerance: Plants have been observed to tolerate temperatures from 15° C. to 35° C.

Disease and pest/insect resistance: Plants have been observed to have tolerance to Power Mildew (*Erysiphe cichoraceaum*).

COMPARISON WITH PARENTAL LINES AND KNOWN VARIETY

'KLEKB20035' is distinguished from its parents as described in Table 1:

TABLE 1

Comparison with Parental Lines

| Characteristic | Variety 'KLEKB20035' | Female parent | Male Parent |
|---|---|---|---|
| Flower colour | Orange with darker orange center | Yellow | Red |
| Doubleness | Semi-double | Double | Single |

'KLEKB20035' can be compared to the commercial variety 'Signal' (unpatented). Differences between the two varieties are described in Table 2:

TABLE 2

Comparison with Similar Variety

| Trait | 'KLEKB20035' | Commercial variety 'Signal' |
|---|---|---|
| Doubleness | Semi-double flowers | Increased doubleness with more petals than 'KLEKB20035'. |
| Colour | Orange flower with darker orange center. | Yellow flower with dark orange center. |

I claim:

1. A new and distinct variety of *Kalanchoe* plant named 'KLEKB20035' as illustrated and described herein.

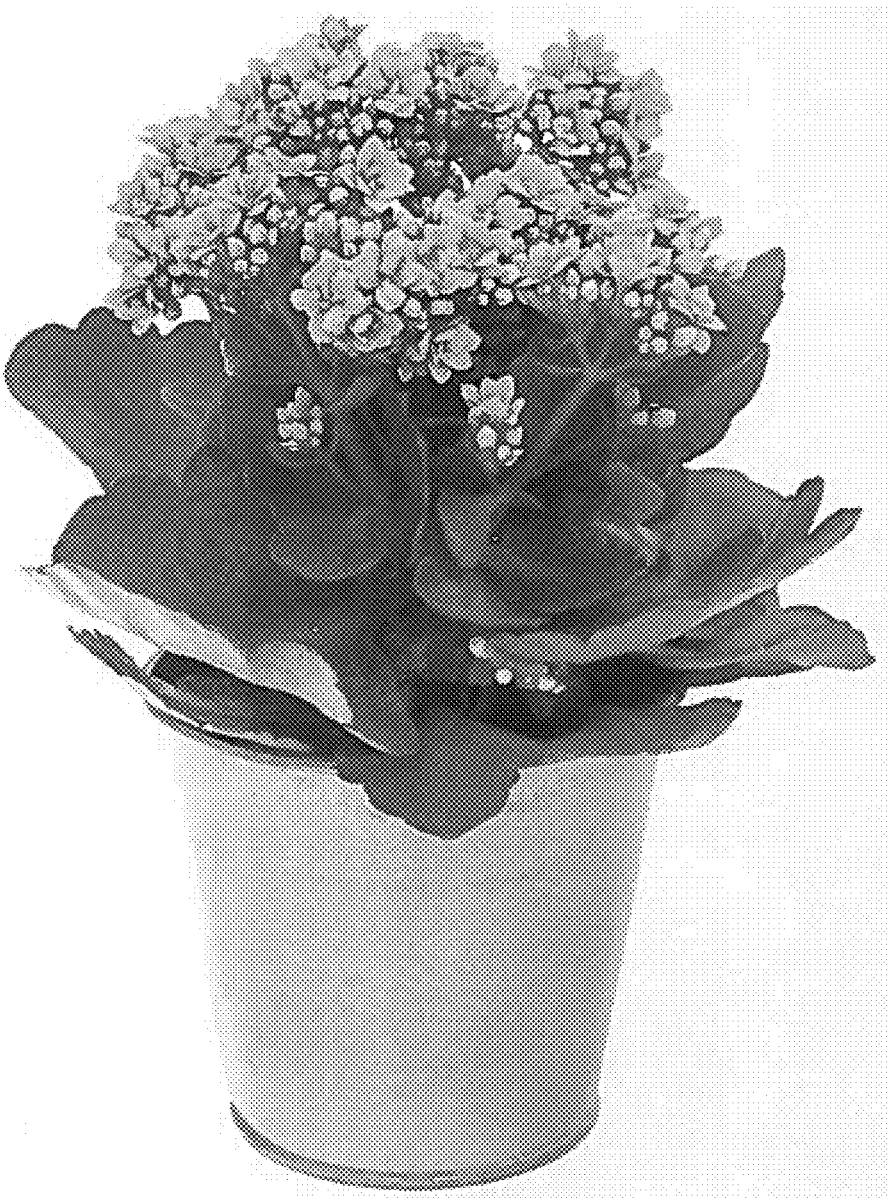

* * * * *